United States Patent
Suzuki

(10) Patent No.: US 11,937,772 B2
(45) Date of Patent: Mar. 26, 2024

(54) OPERATION SWITCH, MEDICAL DEVICE PROVIDED WITH OPERATION SWITCH, AND ENDOSCOPE PROVIDED WITH OPERATION SWITCH

(71) Applicant: OLYMPUS CORPORATION, Tokyo (JP)

(72) Inventor: Masanori Suzuki, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 368 days.

(21) Appl. No.: 17/155,440

(22) Filed: Jan. 22, 2021

(65) Prior Publication Data

US 2021/0169307 A1 Jun. 10, 2021

Related U.S. Application Data

(63) Continuation of application No. PCT/JP2018/029956, filed on Aug. 9, 2018.

(51) Int. Cl.
*A61B 1/00* (2006.01)
*H01H 13/14* (2006.01)
*H01H 13/06* (2006.01)

(52) U.S. Cl.
CPC ...... *A61B 1/00066* (2013.01); *A61B 1/00042* (2022.02); *H01H 13/14* (2013.01); *H01H 13/06* (2013.01)

(58) Field of Classification Search
CPC ............ A61B 1/00066; A61B 1/00042; A61B 1/00052; H01H 13/14; H01H 13/06;

(Continued)

(56) References Cited

U.S. PATENT DOCUMENTS 7,230,196 B2 * 6/2007 Toyama ............... H01H 13/023
200/341
7,420,136 B2 * 9/2008 Goetzl ................... H01H 13/06
200/341

(Continued)

FOREIGN PATENT DOCUMENTS

JP     2003-257274 A     9/2003
JP     2006-004891 A     1/2006

(Continued)

OTHER PUBLICATIONS

International Search Report dated Nov. 13, 2018 received in PCT/JP2018/029956.

*Primary Examiner* — Lheiren Mae A Caroc
(74) *Attorney, Agent, or Firm* — Scully, Scott, Murphy & Presser, P.C.

(57) ABSTRACT

An operation switch includes an elastic operation member, a pressing member, and a switch main body. The elastic operation member is formed of an elastic member, and includes a dome portion on one end side and a circumferential plane portion on the other end side. The dome portion is formed in a dome shape in a natural state, elastically deformed to a balanced state with a predetermined tension different from the natural state, and held as a dome shape. The pressing member moves by deforming the dome portion, and presses an electric switch. The switch main body includes a recess for switch in which an electric switch is disposed, a housing hole in which the pressing member is housed, and a central protrusion around which an inner plane of the circumferential plane portion of the elastic operation member is disposed.

17 Claims, 9 Drawing Sheets

(58) Field of Classification Search
CPC ....... H01H 2009/048; H01H 2300/014; H01H 13/063; H01H 9/04; H01H 2223/002; H01H 2223/04
See application file for complete search history.

(56) References Cited

U.S. PATENT DOCUMENTS

| | | | |
|---|---|---|---|
| 10,256,051 B2 * | 4/2019 | Sanai | A61B 17/320068 |
| 2013/0048482 A1 * | 2/2013 | Saitou | E05B 81/76 200/341 |
| 2017/0105608 A1 | 4/2017 | Kura et al. | |
| 2022/0244751 A1 * | 8/2022 | Kimura | G02B 23/2476 |

FOREIGN PATENT DOCUMENTS

| | | |
|---|---|---|
| JP | 2008-226469 A | 9/2008 |
| JP | 2012-235815 A | 12/2012 |
| WO | 2013/154106 A1 | 10/2013 |
| WO | 2015/198981 A1 | 12/2015 |

* cited by examiner

OPERATION SWITCH, MEDICAL DEVICE PROVIDED WITH OPERATION SWITCH, AND ENDOSCOPE PROVIDED WITH OPERATION SWITCH

CROSS REFERENCE TO RELATED APPLICATION

This application is a continuation application of PCT/JP2018/029956 filed on Aug. 9, 2018, the entire contents of which are incorporated herein by this reference.

BACKGROUND OF THE INVENTION

1. Field of the Invention

The present invention relates to an operation switch including an electric switch that is pressed to be turned on, and an elastic operation member elastically deformed when the switch is pressed, a medical device provided with the operation switch, and an endoscope provided with the operation switch.

2. Description of the Related Art

A medical endoscope generally includes an elongated insertion portion to be inserted into a body cavity, and an operation portion provided in a proximal end side of the insertion portion.

An observation optical system and an illumination optical system are provided at a distal end portion of the insertion portion. Some insertion portions are provided with a bending portion that is freely bendable to improve observation performance and insertability into an inside of a subject. Further, some insertion portions are provided with a fluid conduit to feed air/water into the insertion portion or to suction.

The operation portion is provided with a bending operation device to bend the bending portion. The operation portion is provided with a plurality of press-button switches being electric switches for instructing stopping of an endoscope image, recording of an endoscope image, changing over of illumination lights, and the like. Further, the operation portion is provided with a fluid control button for controlling air feeding, water feeding, and suctioning.

A press type switch device provided to an operation portion main body is illustrated in FIG. 7 or the like of PCT Patent Application No. WO2013/154106. The switch device includes a switch substrate with a switch portion disposed in the operation portion main body and a switch cover to transmit a switch operation of an operator from an outside of the operation portion main body to the switch substrate.

The switch cover includes a base, a cylindrical portion, a first deformable portion, a second deformable portion, and a stress transmission portion, for example. The stress transmission portion includes an operation input portion with a projection-shape and a pressing portion to transmit an inputted outer stress to a switch portion. A main portion of the switch cover is formed by integrally molding a flexible resin or the like. One of the three planes constituting the operation input portion is a pressed plane capable of inputting outer stress caused by the pressing of an operator.

According to the above-described press type switch device, an operator firstly presses the pressed plane of the switch device and inputs an outer stress to the operation input portion. Then, deformation of the first and second deformable portions causes the operation input portion to be tilted, and an end portion of the pressing portion contacts the switch portion. As a result, two contacts (not illustrated) of the switch portion are electrically connected to each other, and the switch device is turned on. When the first pressed plane is released from the pressing, the operation input portion stands up and the switch device returns to an off state.

In recent years, a medical endoscope is subjected to an autoclave sterilization after use. In the autoclave sterilization, the endoscope is left in a chamber. The endoscope in the chamber is sterilized with autoclave sterilization through a pre-vacuum step, a high-pressure steam sterilization step, and a drying step. After the autoclave sterilization, the endoscope is left in an atmosphere.

SUMMARY OF THE INVENTION

An operation switch of an aspect of the present invention includes an elastic operation member, a pressing member, and a switch main body. The elastic operation member is formed of an elastic member with an elastic force and includes: a dome portion having a dome shape provided to one end side of the elastic operation member so as to be located in an outer plane side of a housing through-opening provided to a housing in order to allow an inside of the housing and an outside of the housing to communicate with each other; and a circumferential plane portion having a flange provided to the other end side of the elastic operation member. The dome portion is formed in a dome shape in a natural state, configured to be elastically deformed to a balanced state with a predetermined tension, and held in a dome shape different from the natural state. The pressing member moves by deforming a pressing region of the dome portion inward, and presses an electric switch. The switch main body includes a recess for switch in which the electric switch is disposed, a housing hole in which the pressing member is slidably housed, and a central protrusion having an outer circumferential plane around which an inner plane of the circumferential plane portion of the elastic operation member is disposed.

A medical device according to an aspect of the present invention includes the operation switch in the housing to be grasped by an operator.

An endoscope of an aspect of the present invention includes the operation switch in an operation portion to be grasped by an operator or in a holding base disposed in a proximal end side of the operation portion.

An operation switch of an aspect of the present invention includes: an elastic operation member formed of an elastic member with an elastic force including a dome portion formed as a dome shape protruding outward in a natural state, configured to be elastically deformed in a balanced state with a predetermined tension, and held in a dome shape protruding outward and different from the natural state; a compression member configured to apply force along a plane forming the dome portion such that the dome portion is in the balanced state; and a pressing member configured to be moved by the pressed dome portion.

DETAILED DESCRIPTION OF THE PREFERRED EMBODIMENT

Figure 1:
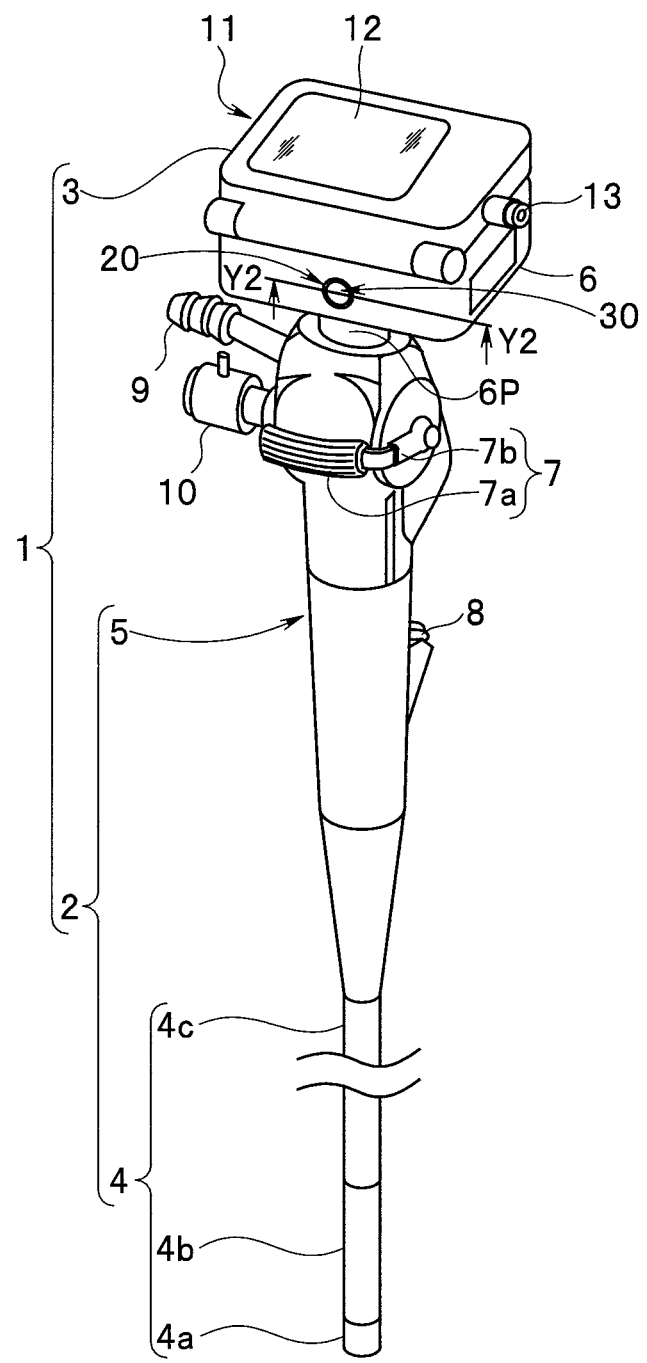
FIG. 1 is a diagram for describing a portable endoscope including an operation switch.

Hereinafter, embodiments of the present invention will be described with reference to the accompanying drawings.

In the drawings used in the following description, in order to make components recognizable in the drawings, some components are different from each other in terms of scale. That is, the present invention is not limited only to the number of the components, the shape of the components, the size ratio of the components, or the relative positional relationship between the components described in these drawings.

An endoscope 1 illustrated in FIG. 1 is a medical device and is a portable endoscope. Main components of the endoscope 1 include an endoscope main body 2 and an image display portion 3.

The endoscope main body 2 includes an elongated insertion portion 4 and an operation portion 5 grasped by an operator. The operation portion 5 is a housing connected to the proximal end side of the insertion portion 4.

Reference numeral 6 denotes an image display portion holding base (hereinafter, simply referred to as a holding base). The holding base 6 is a housing disposed in the proximal end side of the operation portion 5. The holding base 6 is connected to the proximal end side of the operation portion 5 by a coupling pipe 6p. The inside of the holding base 6 and the inside of the operation portion 5 are connected to each other by the coupling pipe 6p.

The insertion portion 4 is inserted into a subject. The insertion portion 4 includes a distal end portion 4a, a bending portion 4b, and a flexible tube portion 4c in this order from the distal end side. The bending portion 4b is bendable in two directions, that is, up and down directions, for example. The flexible tube portion 4c has flexibility.

The operation portion 5 is provided with a bending operation lever 7 for bending the bending portion 4b. The bending operation lever 7 includes a finger hook 7a and an arm 7b. The arm 7b has an L-shape, for example. A finger of an operator is hooked on the finger hook 7a.

The bending portion 4b may be configured to be bendable in four directions, that is, up, down, right, and left directions. In this case, the bending operation lever 7 is provided with an up-down bending operation lever and a right-left bending operation lever.

Reference numeral 8 denotes a treatment instrument insertion port. The treatment instrument insertion port 8 is connected to a treatment instrument channel (not illustrated) passing through the inside of the insertion portion 4. The treatment instrument, such as forceps, is guided to the inside of a body from the treatment instrument insertion port 8 passing through the treatment instrument channel.

In the present embodiment, a light source such as an LED (not illustrated) for emitting illumination light to the inside of the subject is provided in the operation portion 5 of the endoscope 1. The illumination light emitted from the light source is irradiated to the inside of the subject from a distal end plane of the distal end portion 4a through a bundle of optical fibers provided in the insertion portion 4 (not illustrated).

An image pickup apparatus (not illustrated) including an image pickup portion such as a CCD or a C-MOS (not illustrated) and a circuit component (not illustrated) is incorporated in the operation portion 5, the holding base 6, or the insertion portion 4. Further, the operation portion 5 is provided with a suction cap 9 used to suction a liquid such as a body fluid or sputum. A connection tube extending from a suction device (not illustrated) is detachably attached to the suction cap 9.

A first cap is denoted as reference numeral 10 and includes a check valve that opens when the pressure in the operation portion 5 is greater than the outer pressure. Reference numeral 11 denotes an image display portion. The image display portion 11 has an airtight inner space.

A monitor 12 and a second cap 13 are provided to the image display portion 11 attached to the holding base 6. The monitor 12 includes an LCD panel and a cover glass covering a displaying plane of the LCD panel. The second cap 13 includes a vent valve that switches a flow-through state and a shut-off state between the space in the image display portion 11 and the outside thereof.

Reference numeral 20 denotes a power switch. In the present embodiment, the power switch 20 is one of operation switches, and is provided to the holding base 6. Pressing the power switch 20 causes the endoscope 1 to be turned on.

Figure 2:
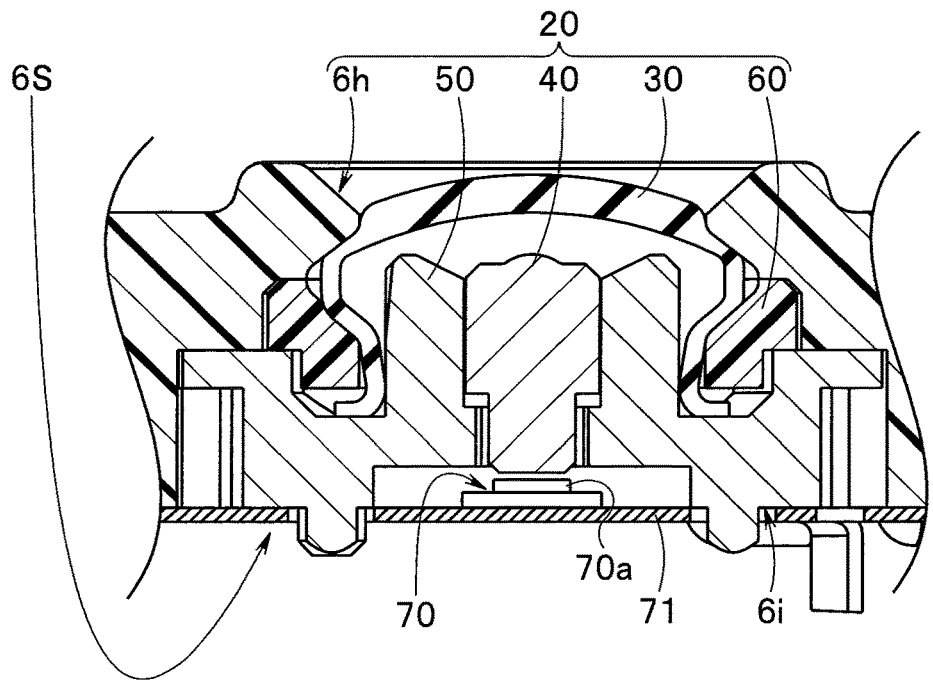
FIG. 2 is a sectional view of the portable endoscope in FIG. 1 taken along line Y2-Y2, and is a diagram for describing a relationship between a holding base and a power switch provided to the holding base.

A holding base through-opening (housing through-opening) (hereinafter, simply referred to as through-opening) 6h that allows a holding base inner space 6S and the outside thereof to communicate with each other is formed in the holding base 6 as illustrated in FIG. 2. The power switch 20 is configured of an operation cover 30, a sliding rod 40 (pressing member), a switch main body 50, and a ring member 60, all of which are integrally disposed in the through-opening 6h.

An electric switch is denoted as reference numeral 70, and is turned on when the sliding rod 40 moves and presses a movable contact 70a. Reference numeral 71 denotes a mounting plate. The mounting plate 71 is fixed at a predetermined position in the inner plane 6i of the holding base inner space 6S. The electric switch 70 is fixed to the mounting plate 71 such that the sliding rod 40 is able to press the movable contact 70a.

Figure 3:
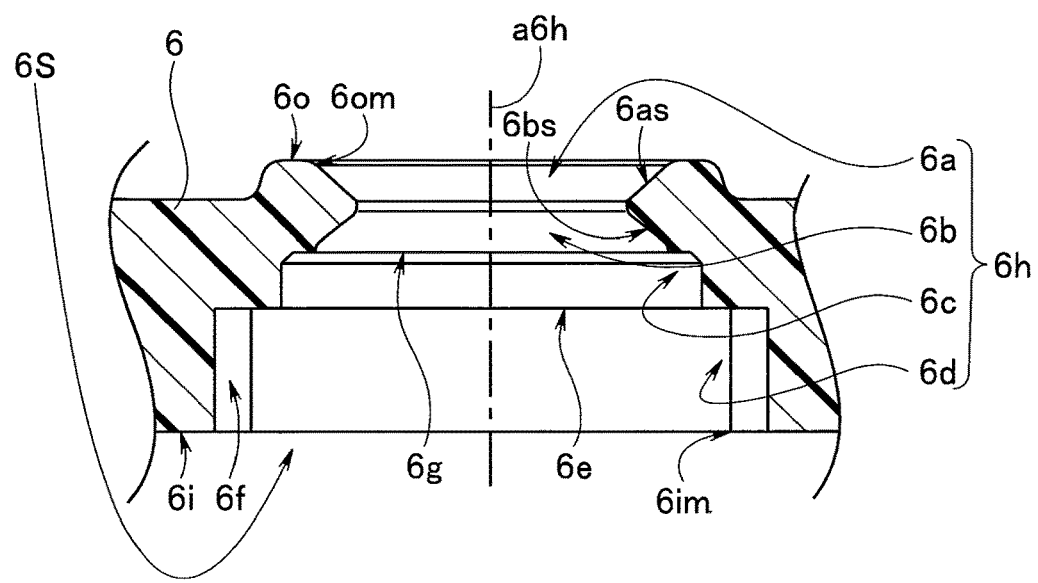
FIG. 3 is a diagram for describing a power switch disposing opening formed in the holding base.

The through-opening 6h in the holding base 6 illustrated in FIG. 3 is a power switch disposing opening. Hereinafter, the through-opening 6h will be described as a power switch disposing opening 6h (simply referred to as disposing opening 6h).

The disposing opening 6h includes a pressing plane exposing portion 6a having a first inclined plane 6as, a dome portion holding portion 6b having a second inclined plane 6bs (second pressing plane), a ring member disposing portion 6c having a bottomed opening, and a switch main body disposing portion 6d in order from the outer plane 6o side.

Reference numeral a6h denotes a central axis of the disposing opening 6h. Reference numeral 6om denotes an outer plane opening, and reference numeral 6im denotes an inner plane opening. Reference numerals 6e and 6g denote bottom planes which will be described later, and reference numeral 6f denotes a recess which will be described later.

Figure 4:
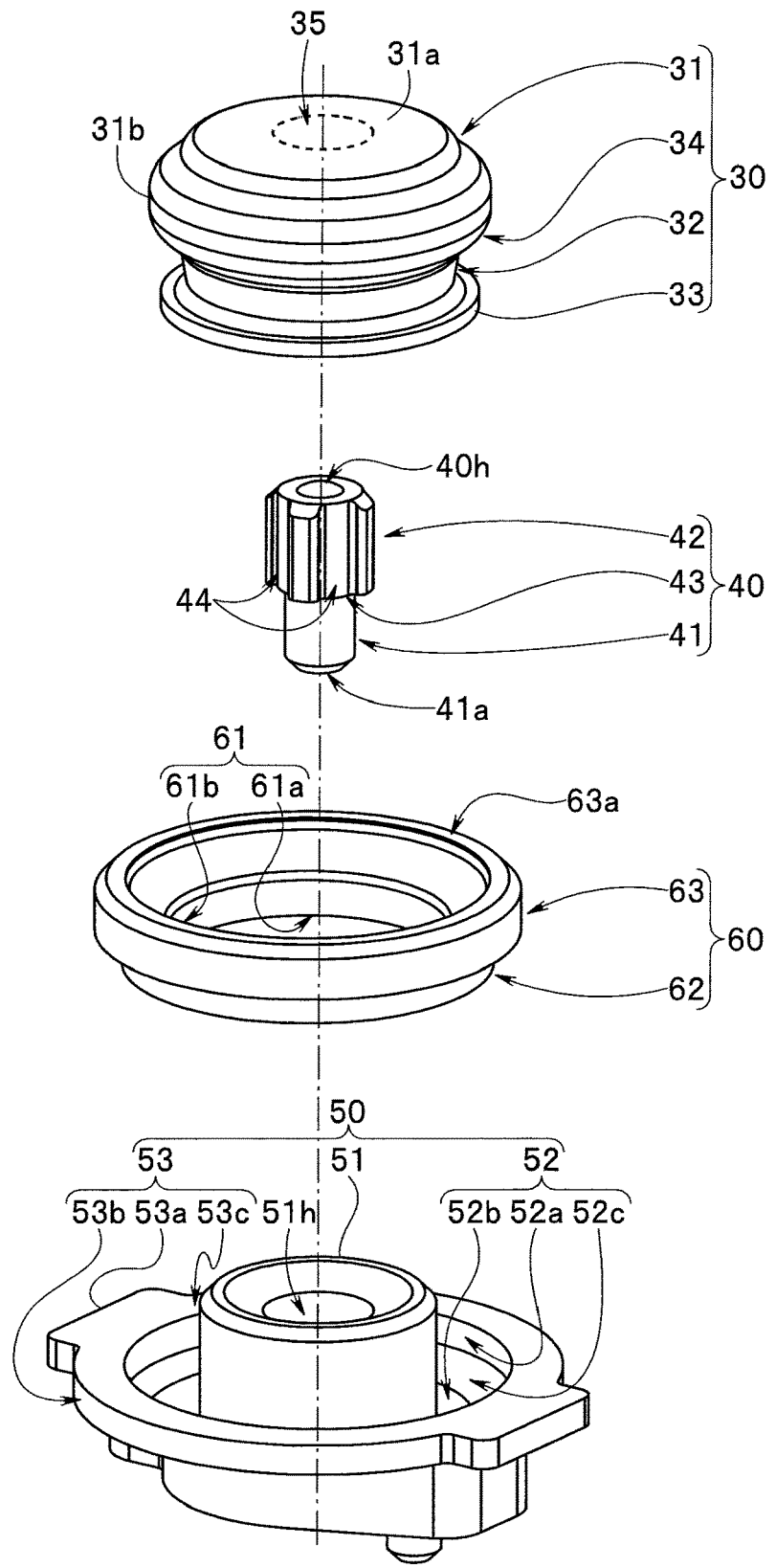
FIG. 4 is an exploded view of a main component of the power switch, and is a perspective view for describing an operation cover, a sliding rod, a switch main body, and a ring member.
Figure 5:
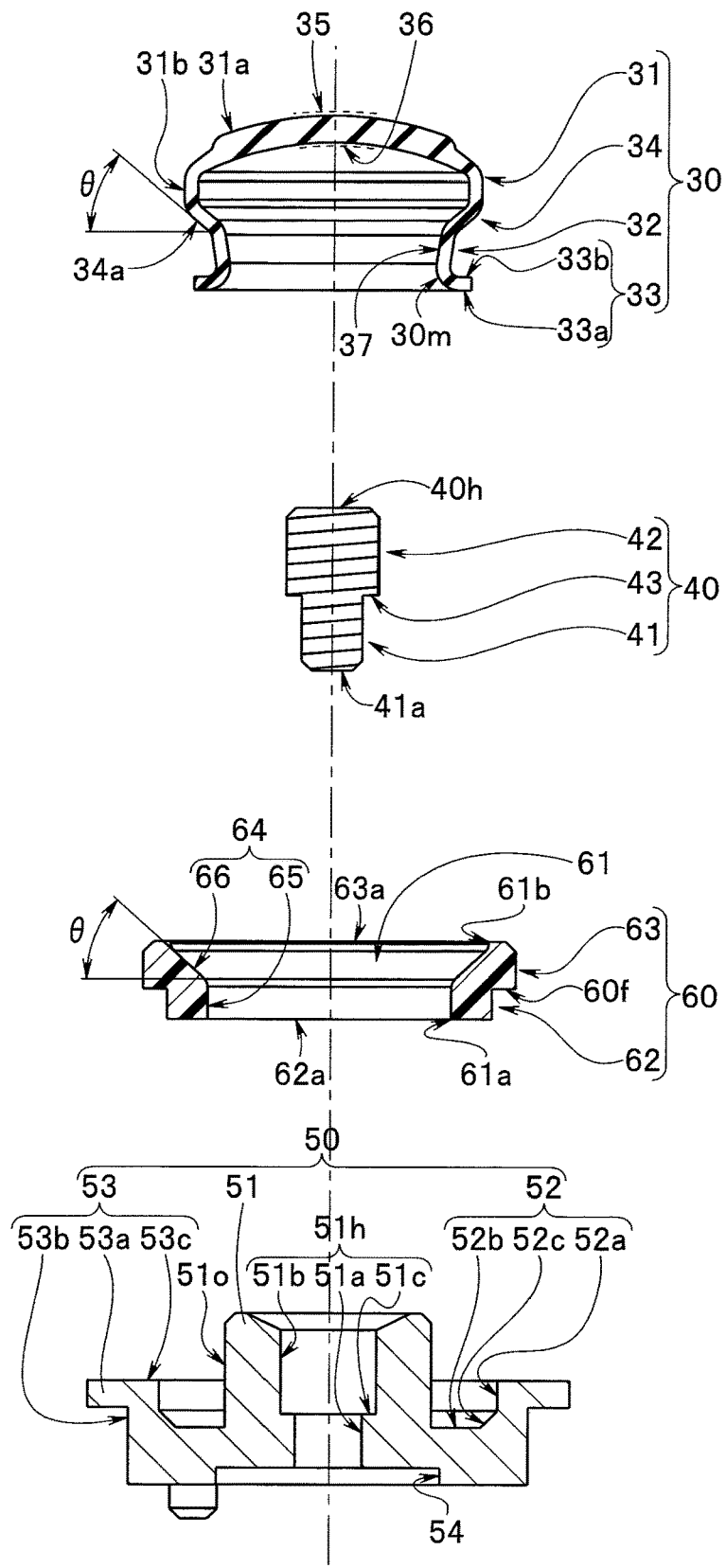
FIG. 5 is an exploded view of the main component of the power switch, and is a perspective view for describing the operation cover, the sliding rod, the switch main body, and the ring member.

The cylindrical operation cover 30, the solid sliding rod 40, the switch main body 50, and the ring member 60 are disposed in the disposing opening 6h as illustrated in FIG. 4 and FIG. 5.

The switch main body 50 includes a central protrusion 51, a circumferential groove 52, and a circular plate portion 53 having a pair of projections 53a. The pair of projections 53a projects outward from the outer circumferential plane 53b. The pair of projections 53a is housed in the recess for projections 6f formed in the switch main body disposing portion 6d of the disposing opening 6h illustrated in FIG. 3.

The central protrusion 51 protrudes from the center of the outward side end plane 53c of the circular plate portion 53. The outward side end plane 53c of the circular plate portion 53 is disposed in contact with the bottom plane for main body disposition 6e of the main body disposition portion 6d.

The circumferential groove 52 is formed to surround the circumference of the central protrusion 51. The circumferential groove 52 is set to a predetermined width and depth. An inclined plane 52c is provided between an outward inner plane 52a and a bottom plane 52b of the circumferential groove 52.

The central protrusion 51 has a housing hole 51h having a stepped shape along the central longitudinal axis. The housing hole 51h is a through-hole having a small diameter hole 51a and a large diameter hole 51b. Reference numeral 51c denotes a stepped plane. The sliding rod 40 is slidably disposed in the housing hole 51h.

Reference numeral 54 in FIG. 5 denotes a recess for switch. The electric switch 70 fixed to the mounting plate 71 is disposed in the recess for switch 54.

The sliding rod 40 illustrated in FIG. 4 and FIG. 5 is rigid. The sliding rod 40 has a small diameter portion 41 and a large diameter portion 42. The small diameter portion 41 is loosely fitted in the small diameter hole 51a. That is, the outer diameter of the small diameter portion 41 is set to be smaller than the inner diameter of the small diameter hole 51a.

On the other hand, the outer diameter of the large diameter portion 42 is set to fit to the inner diameter of the large diameter hole 51b in a predetermined degree. A plurality of cutout grooves 44 is formed at equal intervals in the circumferential direction on an outer circumferential plane of the large diameter portion 42. The cutout groove 44 extends along the central longitudinal axis of the sliding rod 40. The large diameter portion 42 having the cutout groove 44 of the sliding rod 40 is a switch pressing member capable of smoothly moving forward and backward in the large diameter hole 51b of the housing hole 51h. Reference numeral 43 denotes a contact plane. The contact plane 43 contacts the stepped plane 51c.

The sliding rod 40 moves in the housing hole 51h and the movement stops when the contact plane 43 contacts the stepped plane 51c. The distal end plane 41a of the small diameter portion 41 contacts the movable contact 70a of the electric switch 70.

The elastic force of the movable contact 70a causes the sliding rod 40 to be disposed at an initial position.

The contact plane 43 is spaced apart from the stepped plane 51c when the sliding rod 40 is in the initial position. The head 40h of the sliding rod 40 is spaced apart from a sliding rod contact plane 36 of the operation cover 30 by a predetermined distance.

The distal end plane 41a contacting the movable contact 70a moves the movable contact 70a against the elastic force in accordance with the movement of the sliding rod 40.

The electric switch 70 is turned on when the contact plane 43 contacts the stepped plane 51c. The distal end plane 41a of the small diameter portion 41 is a pressing plane.

The operation cover 30 is an elastic operation member with a predetermined rubber hardness formed of an elastic member having elastic force, such as elastic rubber or elastic resin. The operation cover 30 is formed in a predetermined cylindrical shape.

The operation cover 30 mainly includes a dome portion 31 and a circumferential plane portion 32. The dome portion 31 forms one end side of the operation cover 30. The dome portion 31 is disposed on the outer plane opening 6om side of the disposing opening 6h. The circumferential plane portion 32 forms the other end side of the operation cover 30. The circumferential plane portion 32 is provided in the inner plane opening 6im side connecting to the holding base inner space 6S of the disposing opening 6h.

Reference numeral 33 denotes a flange portion, and reference numeral 34 denotes a first inclined portion.

The dome portion 31 mainly has a dome portion outer surface 31a (dome outer surface) and a dome portion outer circumferential portion 31b (dome outer circumferential portion). The dome portion outer circumferential portion 31b is a portion having the largest outer diameter in the dome portion 31. The dome portion outer surface 31a has a dome shape having a curved plane protruding outward from the one end side of the dome portion outer circumferential portion 31b.

The region of the dome portion outer surface 31a indicated by the broken line is a pressing region 35 to be pressed by a finger when the power switch is operated. The pressing region 35 is positioned at a center of the dome portion 31.

The inner plane of the dome portion 31 in the side opposite to the dome portion outer surface 31a is a switch contact plane that can contact the end plane of the central protrusion 51. The switch contact plane is substantially similar to the dome portion outer surface in shape. The area of the inner plane of the dome portion 31 is larger than the area of the dome portion outer surface 31a. The region indicated by reference numeral 36 in the switch contact plane corresponds to the sliding rod contact plane 36. The sliding rod contact plane 36 contacts the head 40*h* of the sliding rod 40.

An outer diameter of the circumferential plane portion 32 is smaller than the outer diameter of the dome portion outer circumferential portion 31*b*. An inner plane 37 of the circumferential plane portion 32 surrounds the outer circumferential plane 51*o* of the central protrusion 51 of the switch main body 50. The inner plane 37 is close to or in contact with the outer circumferential plane 51*o* of the central protrusion 51.

The flange portion 33 (flange) is provided in an opening 30*m* side of the operation cover 30. A flange opening side end plane is denoted as reference sign 33*a* and is positioned in the opening 30*m* side. The flange portion 33 is housed in the circumferential groove 52 of the switch main body 50. The flange opening side end plane 33*a* is disposed on the bottom plane 52*b* of the circumferential groove 52.

Reference numeral 33*b* denotes a flange other end plane. The flange other end plane 33*b* is a plane in the side opposite to the flange opening side end plane 33*a*.

A first inclined portion 34 has an outer inclined plane 34*a* extending from the dome portion outer circumferential portion 31*b* to the circumferential plane portion 32 of the dome portion 31. The first inclined portion pressing plane (first pressing plane, see reference numeral 66 in FIG. 5) of the large diameter ring portion of the ring member 60 (reference numeral 63 in FIG. 4, FIG. 5 and the like), which will be described later, contacts the outer inclined plane 34*a* of the first inclined portion 34. The outer inclined plane 34*a* is an inclined plane having a predetermined acute angle θ.

The ring member 60 is made of resin, for example, and has a through-opening for operation cover (hereinafter, referred to as opening for cover) 61. The operation cover 30 is disposed in the opening for cover 61. The ring member 60 has a small diameter ring portion 62 that is a first ring portion and a large diameter ring portion 63 that is a second ring portion. Reference numeral 60*f* denotes a stepped plane. The stepped plane 60*f* is disposed on the outward side end plane 53*c* of the circular plate portion 53.

An inner plane 64 of the opening for cover 61 has a circumferential plane portion contact plane 65 and a first inclined portion pressing plane 66. The circumferential plane portion contact plane 65 is positioned in the first opening 61*a* side of the small diameter ring portion 62. The first inclined portion pressing plane 66 is positioned in the second opening 61*b* side of the large diameter ring portion 63.

The first inclined portion pressing plane 66 is a first confining plane of the first pressing portion. The first confining plane is an inclined plane having a predetermined acute angle θ.

The small diameter ring portion 62 is housed in the circumferential groove 52 of the switch main body 50. Specifically, the small diameter ring portion 62 is disposed inside the circumferential groove 52 after the flange portion 33 of the operation cover 30 is housed in the circumferential groove 52. Thus, a first opening side end plane 62*a* of the small diameter ring portion 62 is disposed on the flange other end plane 33*b*.

On the other hand, the large diameter ring portion 63 is disposed in the ring member disposing portion 6*c* of the disposing opening 6*h*. Then, the second opening side end plane 63*a* of the large diameter ring portion 63 is disposed in contact with the bottom plane for ring member disposition 6*g*.

The assembling procedure of the power switch 20 will now be described.

Figure 6A:
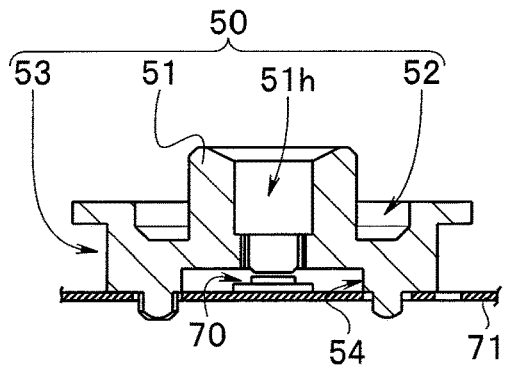
FIG. 6A is a diagram illustrating a mounting plate on which the switch main body with a fixed electric switch is disposed.
Figure 6B:
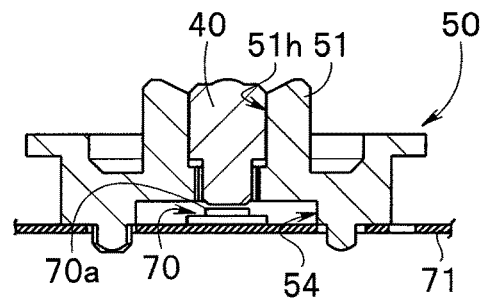
FIG. 6B is a diagram illustrating the sliding rod disposed to a housing hole of the switch main body.

An assembly worker places the switch main body 50 on the mounting plate 71 on which the electric switch 70 is fixed as illustrated in FIG. 6A. The electric switch 70 is provided in a predetermined position in the recess for switch 54. Thereafter, the assembly worker places the sliding rod 40 in the housing hole 51*h* of the switch main body 50 as illustrated in FIG. 6B.

Figure 6C:
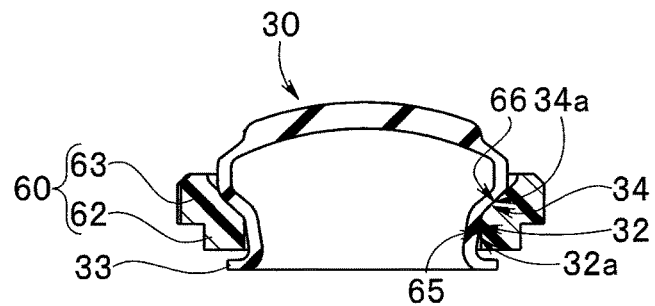
FIG. 6C is a diagram illustrating the ring member attached to the operation cover housed in a circumferential groove of the switch main body.

Next, the assembly worker attaches the ring member 60 to the operation cover 30 as illustrated in FIG. 6C. At this time, the circumferential plane portion contact plane 65 faces a circumferential outer plane 32*a* of the circumferential plane portion 32, and the outer inclined plane 34*a* of the first inclined portion 34 is disposed on the first inclined portion pressing plane 66.

Figure 6D:
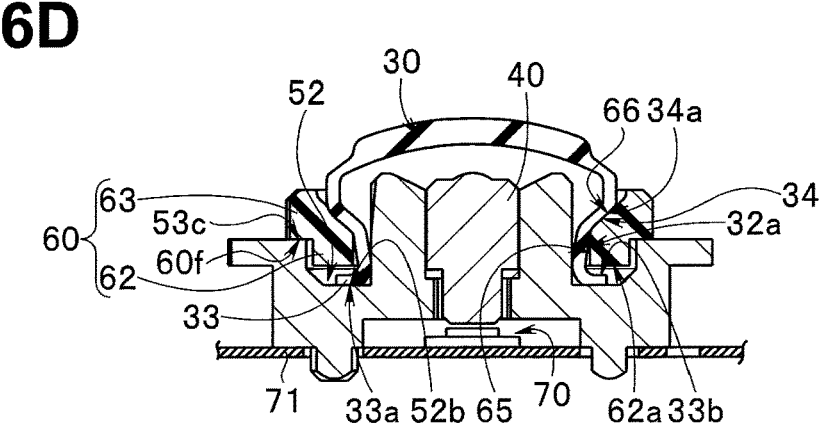
FIG. 6D is a diagram illustrating a switch set obtained by further housing a small diameter ring portion of the ring member in the circumferential groove.

Next, as illustrated in FIG. 6D, the flange portion 33 of the operation cover 30 to which the ring member 60 is attached is housed in the circumferential groove 52 of the switch main body 50. At this time, the flange opening side end plane 33*a* is disposed on the bottom plane 52*b*. After that, the stepped plane 60*f* of the ring member 60 is disposed on the outward side end plane 53*c*, and the small diameter ring portion 62 is housed in the circumferential groove 52. At this time, the first opening side end plane 62*a* is disposed on or faces the flange other end plane 33*b*.

As a result, a switch set s20 is formed in which the electric switch 70, the operation cover 30, the sliding rod 40, and the ring member 60 are disposed in the switch main body 50.

Figure 6E:
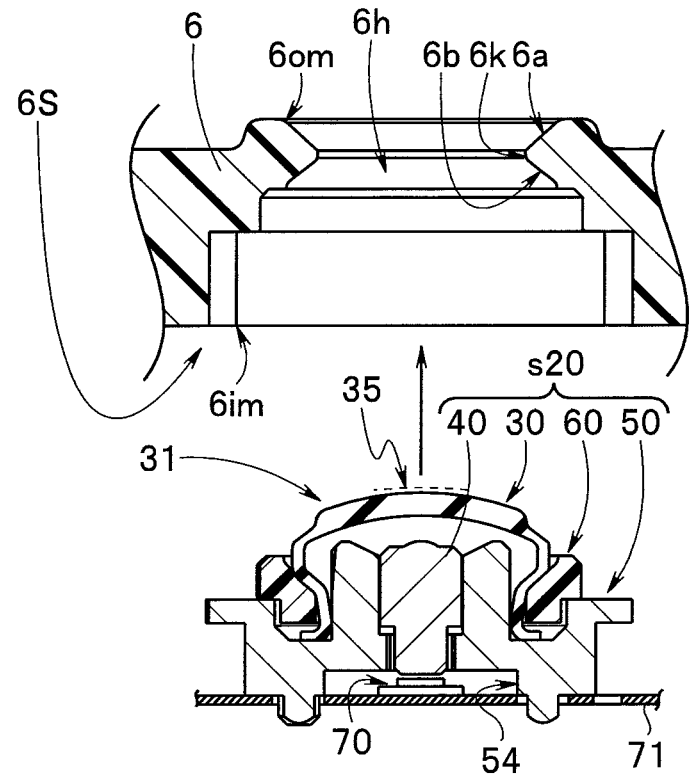
FIG. 6E is a diagram for describing a relationship between the switch set and a disposing opening of the holding base.

Next, the assembly worker introduces the switch set s20 from the inner plane opening 6*im* of the disposing opening 6*h* of the holding base 6 toward the outer plane opening 6*om* as indicated by the arrow in FIG. 6E. At this time, the assembly worker introduces the switch set s20 toward the deeper side of the disposing opening 6*h* while observing the positional relationship between the outer plane opening 6*om* and the pressing region 35 of the dome portion 31. The positional relationship is observed from the outer plane opening 6*om* side of the disposing opening 6*h* of the holding base 6.

Figure 6F:
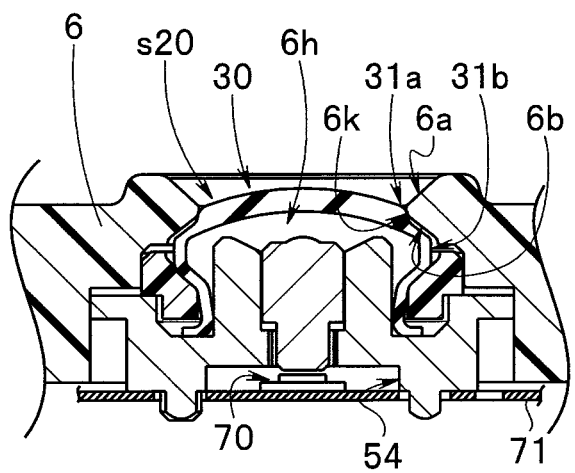
FIG. 6F is a diagram illustrating that an entire circumference of an outer circumferential portion of a dome portion included by the switch set introduced into the disposing opening is in contact with a boundary portion.

Then, the dome portion outer circumferential portion 31*b* side of the dome portion outer surface 31*a* contacts the boundary portion 6*k* between the pressing plane exposing portion 6*a* and the dome portion holding portion 6*b* over the entire circumference as illustrated in FIG. 6F, and the introduction of the switch set s20 into the disposing opening 6*h* is temporarily halted.

Figure 6G:
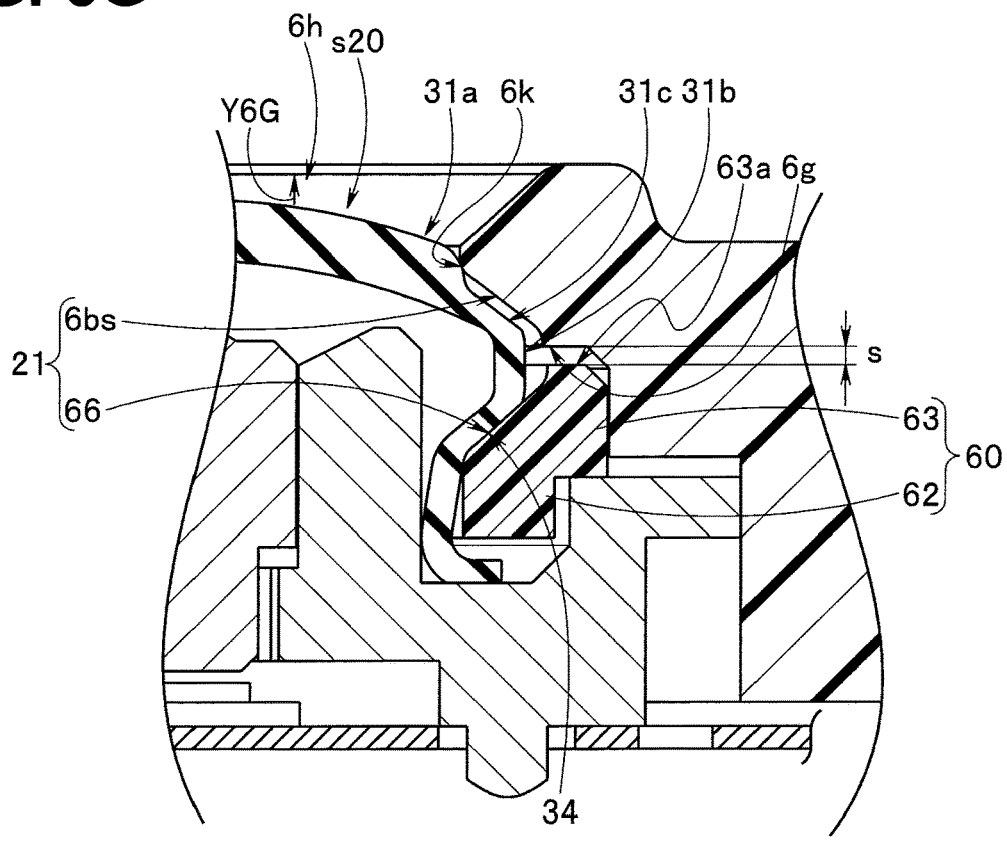
FIG. 6G is an enlarged view of part of FIG. 6F, and is a diagram for describing a state in which a space is formed between a second opening side end plane and a bottom plane for ring member disposition.

At this time, as illustrated in FIG. 6G, the second opening side end plane 63*a* of the large diameter ring portion 63 is positioned close to the bottom plane for ring member disposition 6*g* of the ring member disposing portion 6*c*. In other words, the second opening side end plane 63*a* and the bottom plane for ring member disposition 6*g* face each other with a slight space s interposed therebetween.

Thereafter, the assembly worker further pushes the switch set s20 against the elastic force of the operation cover 30 toward the deeper side of the disposing opening 6*h* indicated by arrow Y6G. Then, the first inclined portion 34 and the dome portion outer circumferential portion 31*b* positioned on the first inclined portion pressing plane 66 are also moved toward the deeper side.

Figure 6H:
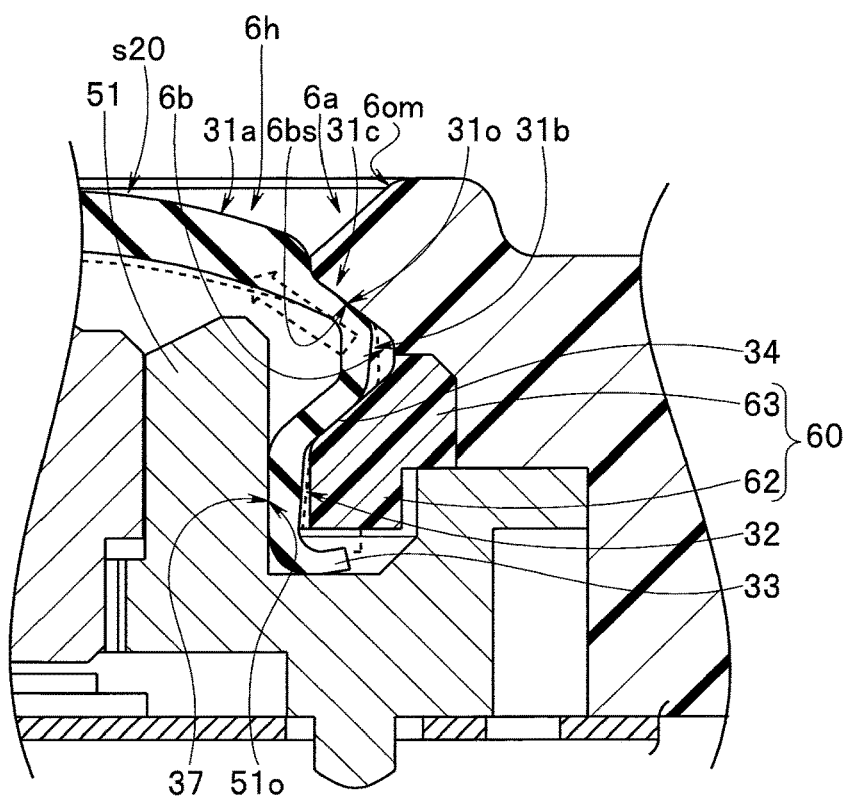
FIG. 6H is a diagram illustrating the switch set reaching a deeper side of the disposing opening against elastic force of the dome portion, and is a diagram for describing a state in which the dome portion is elastically deformed from a natural state.

Then, as illustrated in FIG. 6H, the switch set s20 reaches the predetermined position in the disposing opening 6*h* while the outer inclined plane 31*o* of the second inclined portion 31*c* positioned between the dome portion outer surface 31*a* and the dome portion outer circumferential portion 31*b* comes into contact with the second inclined plane 6*bs* of the dome portion holding portion 6*b*.

When the switch set s20 reaches the predetermined position while the outer inclined plane 31*o* comes into contact with the second inclined plane 6*bs*, the dome portion outer circumferential portion 31*b*, the first inclined portion 34, and the circumferential plane portion 32 are elastically deformed from the natural state indicated by the broken line in FIG. 6H.

As a result, the outer inclined plane 31*o* of the second inclined portion 31*c* comes into close contact with the second inclined plane 6*bs*, and the inner plane 37 of the circumferential plane portion 32 comes into contact with or comes into close contact with the outer circumferential plane 51*o* of the central protrusion 51.

The outer inclined plane 31*o* of the second inclined portion 31*c* comes into contact with the second inclined plane 6*bs* and is pressed to change into a close contact state. When the change occurs, the second inclined portion 31*c* is compressed in the direction indicated by the broken line arrow and is deformed as illustrated by the solid line from the natural state illustrated by the broken line.

That is, the second inclined plane 6*bs* has a function as a second confining plane of the second pressing portion that compresses and deforms the second inclined portion 31*c*.

When the switch set s20 reaches the predetermined position, the pressing force to the outer inclined plane 34*a* of the first inclined portion 34 by the first inclined portion pressing plane 66 is maintained, and at the same time the compression of the second inclined portion 31*c* by the second inclined plane 6*bs* is maintained.

As illustrated in FIG. 6G, when the second opening side end plane 63*a* closely faces the bottom plane for ring member disposition 6*g*, a V-shaped confining portion 21 is formed by the first inclined portion pressing plane 66 (first pressing plane) facing the first inclined portion 34 and the second inclined plane 6*bs* (second pressing plane). The ring member 60 having the first inclined portion pressing plane 66 (first pressing plane) and the holding base 6 having the second inclined plane 6*bs* (second pressing plane) are compression members.

When the switch set s20 is pushed toward the deeper into the disposing opening 6*h*, the confining portion 21 causes the outer inclined plane 31*o* of the second inclined portion 31*c* of the dome portion outer surface 31*a* to contact the second inclined plane 6*bs*.

Further, the confining portion 21 presses the outer inclined plane 31*o* of the second inclined portion 31*c* in contact therewith, and compresses the second inclined portion 31*c* in the direction of the pressing region 35 of the dome portion 31 (direction indicated by broken line arrow) from the outer circumferential end side.

With this, the dome portion 31 in the pressing plane exposing portion 6*a* is balanced with a predetermined tension (held in balanced state) and is elastically deformed to a dome shape protruding outward (held in dome shape protruding outward) different from the natural state. The compression member compresses the dome portion 31 toward the center of the dome portion 31 to make the balanced state.

After that, the mounting plate 71 is fixed to the inner plane 6*i* of the holding base 6 by a fixing screw (not illustrated). With this, the power switch 20 is disposed to the holding base 6 as illustrated in FIG. 2 described above without the use of an adhesive agent. Thus, the rubber hardness of the operation cover 30 is maintained without change. That is, in the power switch 20, the pressing force to the outer inclined plane 34*a* of the first inclined portion 34 by the first inclined portion pressing plane 66 continues to be maintained, and the compression of the second inclined portion 31*c* by the second inclined plane 6*bs* continues to be maintained.

Here, the operation of the power switch 20 will be described.

Figure 7:
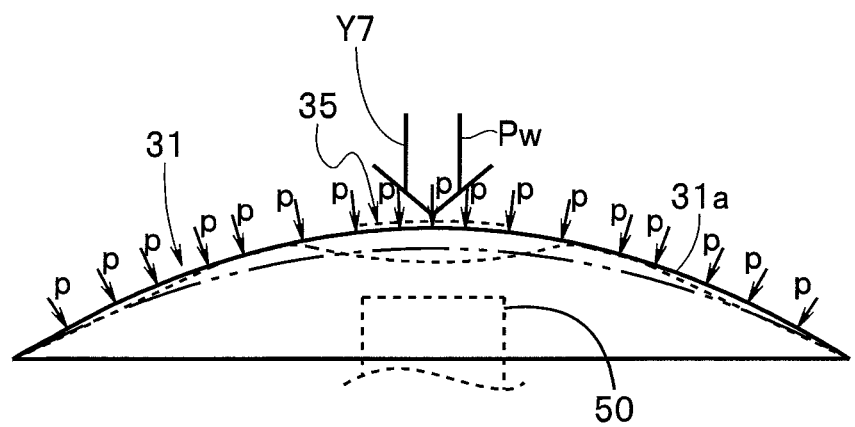
FIG. 7 is a diagram for describing an action of the dome portion having a dome shape different from the natural state by being compressed and elastically deformed.

The dome portion 31 of the power switch 20 is curved outward in the balanced state with a predetermined tension different from the natural state. The dome portion 31 in the balanced state receives the outside air pressure on the entire surface of the dome portion outer surface 31*a* as illustrated in FIG. 7 until the pressure difference between the outer air pressure and the pressure in the endoscope, which is the pressure in the dome portion 31, after the completion of the autoclave sterilization reaches a predetermined pressure P. The outer air pressure is dispersed to p and the balanced state is maintained, and thus, the dome portion 31 maintains the curved shape protruding outward while elastically deforms as illustrated by the dashed-and-double-dotted line.

When the pressure difference exceeds P, the balance is broken and the dome portion 31 is retracted.

The pressure difference P is set in advance to be higher than the pressure difference Pa in which the switch cover of the press type switch device described in the above-described publication is retracted after the completion of the autoclave sterilization. In addition, the pressure difference P is set in advance to be higher than the pressure difference Pb in which a switch cover having a reduced flexibility is retracted. The reduced flexibility is aimed to avoid a problem that the switch cover is retracted.

Therefore, even when the pressure differences Pa and Pb are generated on the dome portion outer surface 31*a*, the dome portion 31 maintains the dome shape different from the natural state.

Figure 8:
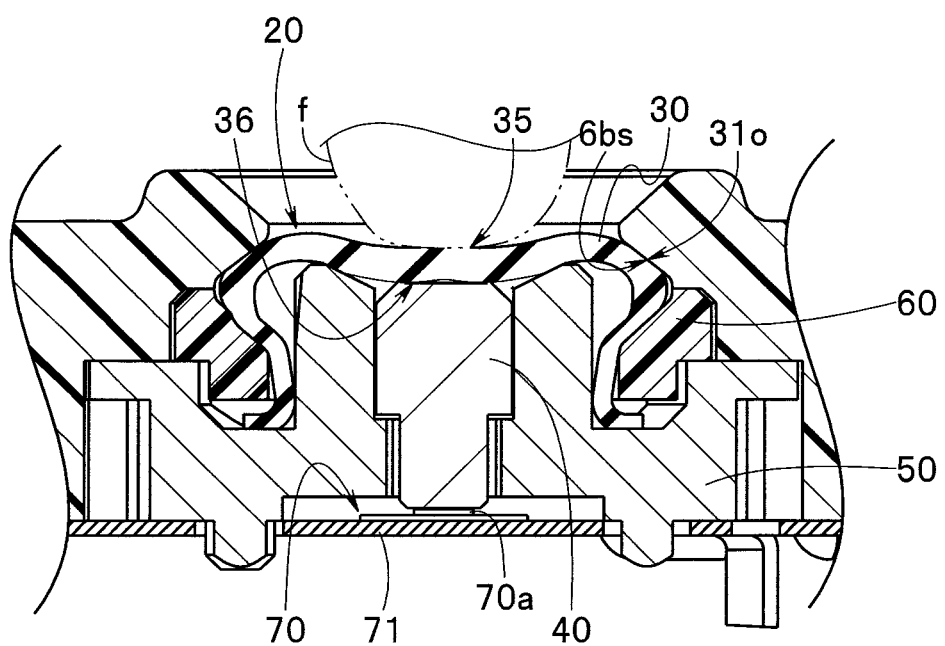
FIG. 8 is a diagram for describing the power switch operated by a finger.

On the other hand, when the user performs observation by the endoscope 1, the user operates the power switch 20. The user presses the pressing region 35 of the operation cover 30 with a finger f as illustrated in FIG. 8.

At this time, the pressing region 35 of the dome portion outer surface 31*a* is pressed as indicated by arrow Y7 by the pressing force of Pw as illustrated in FIG. 7. The dome portion 31 with the predetermined tension different from the natural state maintains the dome shape different from the natural state until the force amount of the pressing force reaches predetermined force amount Pp.

Figure 9:
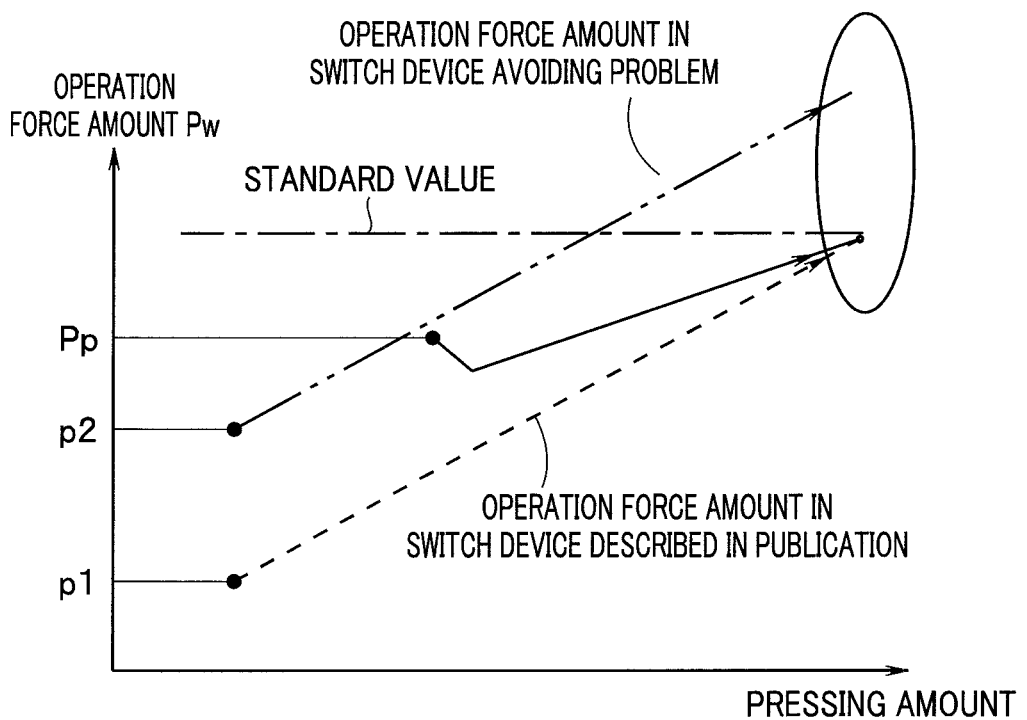
FIG. 9 is a diagram for describing a relationship between an operation force amount and a pressing amount.

In other words, the dome portion 31 maintains curving outward until the force amount of the pressing force reaches Pp as illustrated in FIG. 9.

The force amount Pp is larger than the initial operation force amount p1 of the press type switch device described in the above-described publication, and is larger than the initial operation force amount p2 of the press type switch device avoiding a problem that the switch cover is retracted.

As indicated by the broken line in FIG. 9, in a press type switch device described in the publication, the electric switch is turned on when the operation force amount Pw reaches the standard value, for example. On the other hand, as indicated by the dashed-and-double-dotted line, in the press type switch device avoiding the problem that the switch cover is retracted, the electric switch is turned on when the operation force amount Pw exceeds the standard value by far.

The dome portion 31 is held in the curved shape without elastically deforming until the operation force amount Pw exceeds Pp as illustrated in FIG. 9. When the operation force amount Pw exceeds Pp, the balance in the vicinity of the pressing region 35 is broken and the dome portion 31 deforms as indicated by the broken line in FIG. 7.

When the balance is broken, the sliding rod contact plane 36 of the dome portion 31 is brought closer to the head 40h of the sliding rod 40 with a force amount smaller than Pp as indicated by the solid line in FIG. 9. After the sliding rod contact plane 36 reaching the head 40h, the pressing of the sliding rod 40 by the user begins as indicated by the solid line in FIG. 9.

As a result, the sliding rod 40 is moved, and the movement of the sliding rod 40 causes the movable contact 70a of the electric switch 70 to be deformed and the electric switch 70 is turned on.

As indicated by the oblong ellipse in FIG. 9, the operation force amount Pw when the electric switch 70 is turned on is set to be equal to or less than a predetermined value. Further, when the user moves the finger f away from the operation cover 30, the operation cover 30 is restored to the original curved shape, and the movable contact 70a returns to the original position and the electric switch 70 is turned off.

As described above, the dome portion 31 of the power switch 20 is compressed and is formed into a dome shape curved outward with a predetermined tension different from the natural state so that the dome portion 31 is not retracted until a pressure difference reaches the pressure difference P higher than the pressure differences Pa and Pb.

As a result, it is possible to more reliably prevent a problem that the retraction of the dome portion 31 of the power switch 20 causes the power switch 20 to be turned on in the endoscope 1 after the completion of the autoclave sterilization.

Further, when the power switch 20 is operated, the initial operation force amount Pp to deform the dome portion 31 is larger than the initial operation force amount p1 of the press type switch device described in the above-described publication, and the initial operation force amount p2 of the press type switch device provided with an improved switch cover that enables to avoid the problem. However, when the power switch 20 is turned on, the initial operation force amount Pp is within the standard value in a similar way as the operation force amount of the press type switch device in the past.

As a result, it is possible to achieve a power switch having excellent operability while preventing the switch device from being turned on because of a pressure difference generated between the outer air and the inside of the endoscope during leaving the switch device in an atmosphere after the completion of the autoclave sterilization.

Further, in the power switch 20, when the sliding rod 40 is in the initial position, the head 40h of the sliding rod 40 is separated from the sliding rod contact plane 36 of the operation cover 30 by a predetermined distance. The sliding rod 40 is slidably disposed in the housing hole 51h.

With this, when the dome portion 31 of the operation cover 30 is deformed as set in advance, the sliding rod 40 is moved. Thus, the electric switch 70 may be uniformly operated by the operation of the power switch 20.

The pressing force to the outer inclined plane 34a of the first inclined portion 34 by the first inclined portion pressing plane 66 continues to be maintained, and the compression of the second inclined portion 31c by the second inclined plane 6bs continues to be maintained in the power switch 20. Accordingly, the outer inclined plane 31o of the second inclined portion 31c comes into close contact with the second inclined plane 6bs of the dome portion holding portion 6b during the operation of the power switch 20, and thus, water tightness against the outside is reliably ensured.

Note that, in the press type switch device provided with the above-described improved switch cover, the operation force amount exceeds the standard value when the electric switch is turned on as indicated by the dashed-and-double-dotted line in FIG. 9.

In the present embodiment, the operation switch provided to the holding base 6 of the endoscope 1 serves as the power switch 20. However, the operation switch is not limited to the power switch of the endoscope 1, and may be a freeze switch for generating a freeze signal, a release switch for generating a release signal, and an electric switch for outputting an electric signal such as an observation mode changeover switch provided in the operation portion of an endoscope, for example. Further, the operation switch may be a power switch or an electric switch provided to the housing of a medical device other than an endoscope.

The present invention is not limited to the embodiments described above, and various changes and modifications can be made without departing from the spirit and scope of the present invention.

What is claimed is:

1. An operation switch comprising:
  an elastic cover comprising a first inclined portion extending in a direction of an axis from a first radial position away from the axis towards the axis; and
  one or more contact portions,
  wherein the first inclined portion of the elastic cover is pressed by a housing and the one or more contact portions towards the axis to elastically deform the elastic cover and protrude a pressing region of the elastic cover through an opening of the housing,
  wherein the one or more contact portions comprises a first ring portion and a second ring portion, and
  wherein a diameter of the first ring portion is smaller than a diameter of the second ring portion.

2. A medical device comprising:
  the operation switch according to claim 1; and
  the housing,
  wherein the operation switch is provided to the housing.

3. An endoscope comprising:
  an operation portion configured to be grasped by an operator; and
  the operation switch according to claim 1,
  wherein the operation switch is provided to the operation portion or in a proximal end side of the operation portion.

4. The operation switch according to claim 1,
  wherein the elastic cover comprises a dome portion protruding outward in a natural state, and
  wherein the first inclined portion of the elastic cover is pressed by the housing and the one or more contact portions so the pressing region is elastically deformed to a dome shape in a balanced state being different from the natural state, and having a predetermined tension and protruding through the opening of the housing.

5. The operation switch according to claim 4, further comprising:
  the housing,
  wherein the housing defines an inner space and the opening allowing the inner space and an outside to communicate with each other,
  wherein the one or more contact portions are disposed in the inner space, and
  wherein the elastic cover is partially arranged in the inner space with the pressing region of the elastic cover protruding through the opening of the housing.

6. The operation switch according to claim 4, further comprising:

a pressing portion configured to be moved by a force transmitted through the pressing region of the elastic cover; and an electric switch configured to be pressed by the pressing portion.

7. The operation switch according to claim 4, wherein the axis extends through a center of the dome shape, the first radial position of the first inclined portion is arranged at a portion of the dome shape having a largest outer diameter, and the pressing region is arranged at a top of the dome shape, and wherein the first inclined portion of the elastic cover is pressed by the housing and the one or more contact portions towards the center of the dome shape to elastically deform the elastic cover to protrude the pressing region of the elastic cover through the opening of the housing.

8. The operation switch according to claim 1, wherein the elastic cover comprises:

a dome portion provided to one side of the elastic cover along the axis, wherein the dome portion comprises the first inclined portion and the pressing region; and a circumferential plane portion comprising a flange provided to another side of the elastic cover along the axis, wherein the first inclined portion of the elastic cover is pressed by the housing and the one or more contact portions towards the axis to elastically deform the dome portion of the elastic cover from a first dome shape in a natural state to a second dome shape in a balanced state with a predetermined tension.

9. The operation switch according to claim 8, further comprising:

an electric switch;

a pressing portion configured to be moved to press the electric switch by deforming the pressing region of the elastic cover inward toward the housing; and a switch main body defining a recess in which the electric switch is disposed and a housing hole in which the pressing portion is slidably housed, and comprising a central protrusion having an outer circumferential plane around which an inner plane of the circumferential plane portion of the elastic cover is disposed.

10. The operation switch according to claim 9, wherein the one or more contact portions comprises:

a ring comprising:

the first ring portion provided to the switch main body; and the second ring portion, and wherein the dome portion is pressed by a first pressing plane of the second ring portion and a second pressing plane of the housing to elastically deform the elastic cover and protrude the pressing region of the elastic cover through the opening of the housing.

11. The operation switch according to claim 10, wherein the elastic cover comprises a second inclined portion extending in a direction of the axis from a second radial position, closer to the axis than the first radial position, towards the first radial position, and wherein the second inclined portion of the elastic cover is pressed by the first pressing plane of the second ring portion towards the axis and as a result the second inclined portion together with the housing presses the first inclined portion of the elastic cover towards the axis to elastically deform the elastic cover and protrude the pressing region of the elastic cover through the opening of the housing.

12. The operation switch according to claim 11, wherein, when the pressing portion is moved by deforming the pressing region of the elastic cover inward toward the housing, a pressing force to the second inclined portion by the first pressing plane of the second ring portion is maintained and a compression of the first inclined portion of the elastic cover by the housing is maintained.

13. The operation switch according to claim 8, wherein the dome portion is configured to maintain a curved shape curving outward from the opening of the housing in the balanced state until a pressure difference between an air pressure outside the dome portion and an air pressure inside the dome portion reaches a predetermined pressure, and wherein the dome portion is configured to retract from the curved shape in response to the pressure difference exceeding the predetermined pressure.

14. The operation switch according to claim 8, wherein the dome portion is configured to maintain the curved shape in the balanced state until a force amount pressing the pressing region reaches a predetermined force amount, and wherein the dome portion is configured to retract from the curved shape in response to the force amount exceeding the predetermined force amount.

15. The operation switch according to claim 8, wherein the dome portion comprises:

a dome outer surface having a curved plane protruding outward from the opening of the housing, the dome outer surface comprising the pressing region; and a dome inner surface having a substantially similar shape as the dome outer surface, wherein an area of the dome inner surface is larger than an area of the dome outer surface.

16. An operation switch comprising:

a holding base;

a switch main body disposed inside the holding base, the switch main body comprising a tubular protrusion extending in a longitudinal direction, the tubular protrusion forming a hole inside;

a pressing body disposed in the hole and configured to move along the longitudinal direction to press an electric switch; and an elastic cover configured to cover the switch main body and the pressing body, the elastic cover comprising:

a dome portion provided to a first side of the elastic cover; and a flange provided to a second side of the elastic cover, wherein the dome portion comprises a first inclined surface pressed inward of the holding base to be deformed with a tension, a ring comprising a first ring portion provided on the switch main body, and a second ring portion provided on the holding base, wherein a second inclined surface of the elastic cover is pressed by the second ring portion to deform with a tension.

17. The operation switch according to claim 16, wherein when the pressing body is moved by deforming a pressing region of the elastic cover inward toward the holding base, a pressing force to the second inclined surface by the second ring portion is maintained, and a compression of the first inclined surface of the elastic cover by the holding base is maintained.

* * * * *